United States Patent
Everhart et al.

(10) Patent No.: US 7,700,360 B2
(45) Date of Patent: Apr. 20, 2010

(54) OPTICAL METHOD AND SYSTEM TO DETERMINE DISTRIBUTION OF LIPID PARTICLES IN A SAMPLE

(75) Inventors: Dennis S. Everhart, Alpharetta, GA (US); Jack N. Lindon, Alpharetta, GA (US); Luis Garcia-Rubio, Temple Terrace, FL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1097 days.

(21) Appl. No.: 11/067,773

(22) Filed: Feb. 28, 2005

(65) Prior Publication Data
US 2005/0233439 A1 Oct. 20, 2005

Related U.S. Application Data

(60) Provisional application No. 60/626,045, filed on Nov. 8, 2004, provisional application No. 60/563,614, filed on Apr. 20, 2004.

(51) Int. Cl.
*G01N 33/92* (2006.01)
*G01N 33/48* (2006.01)
*G01N 21/63* (2006.01)

(52) U.S. Cl. .......................... 436/71; 436/63; 436/164; 436/165; 436/171; 422/82.05; 422/82.09; 356/51; 356/300; 356/317; 356/318; 356/335; 356/336; 356/337; 356/338; 356/340; 356/432; 356/436

(58) Field of Classification Search .................. 436/63, 436/71, 164, 165, 171; 422/82.05, 82.09; 356/51, 300, 317, 318, 319, 335, 336, 337, 356/338, 340, 343, 432, 436; 435/287.2; 702/19

See application file for complete search history.

(56) References Cited

U.S. PATENT DOCUMENTS 5,246,864 A * 9/1993 Purdie .......................... 436/71

(Continued)

FOREIGN PATENT DOCUMENTS

WO WO-0204947 A2 1/2002

(Continued)

OTHER PUBLICATIONS

Alupoaei, C M., et al., "Growth behavior of microorganisms using UV-Vis spectroscopy: *Escherichia coli*", *Biotechnol Bioeng.*, 86(2), (Apr. 20, 2004), 163-7.

(Continued)

*Primary Examiner*—Maureen M Wallenhorst
(74) *Attorney, Agent, or Firm*—Armstrong Teasdale LLP

(57) ABSTRACT

The system and method of the present invention relate to characterizing lipoproteins in a sample. The system includes a light source that delivers electromagnetic energy in a predetermined range of wavelengths to the sample and a sensor that senses an intensity spectrum which emerges from the sample when the sample is illuminated by the light source. A processor determines a chemical composition of the sample to determine the presence of lipoprotein particles. The processor then characterizes lipoproteins that are within in the sample by deconvoluting the intensity spectrum into a scattering spectrum and absorption spectrum. The method includes illuminating the sample with electromagnetic energy having a predetermined range of wavelengths and sensing the electromagnetic energy that emerges from the sample. The method further includes transducing the sensed electromagnetic energy which emerges from the sample into an intensity spectrum that determines the types of lipoproteins that are within the sample.

19 Claims, 13 Drawing Sheets

U.S. PATENT DOCUMENTS

| | | | | |
|---|---|---|---|---|
| 5,252,488 | A | * | 10/1993 | Purdie .......................... 436/71 |
| 5,417,863 | A | | 5/1995 | Varady et al. |
| 5,589,932 | A | | 12/1996 | Garcia-Rubio et al. |
| 5,808,738 | A | | 9/1998 | Garcia-Rubio |
| 6,330,058 | B1 | | 12/2001 | Garcia-Rubio et al. |
| 6,737,275 | B2 | * | 5/2004 | Purdie et al. .................. 436/71 |
| 6,797,518 | B1 | * | 9/2004 | Jacobs et al. .................. 436/46 |
| 7,022,527 | B2 | * | 4/2006 | Liu et al. ...................... 436/71 |
| 2001/0024800 | A1 | | 9/2001 | Garcia-Rubio et al. |

FOREIGN PATENT DOCUMENTS

| | | |
|---|---|---|
| WO | WO-02075286 A1 | 9/2002 |
| WO | WO-03023397 A1 | 3/2003 |

OTHER PUBLICATIONS

Alupoaei, C M., et al., "Quantitative spectroscopy analysis of prokaryotic cells: vegetative cells and spores", *Biosens Bioelectron.*, 19(8), (Mar. 15, 2004), 893-903.

Dersch, M, "Electrospinning of Nanostructured Composite Fibers", *New Frontiers in Fiber Science, Spring Meeting,* (May 23-25, 2001).

Gibson, Phillip , "Changes in Porosity and Transport Properties of Microporous Elastomeric Electrospun Nonwoven Membranes Under Biaxial Strain Conditions", *New Frontiers in Fiber Science, Spring Meeting,* (May 23-25, 2001).

Hou, H, "Preparation of oriented nano- and mesotubes by electrospun template fibers (TUFT-process)", *New Frontiers in Fiber Science, Spring Meeting,* (May 23-25, 2001).

Liu, W, "Surface Coating of Poly(meta-phenylene isophthalamide) Nanofibers", *New Frontiers in Fiber Science, Spring Meeting,* (May 23-25, 2001).

Reneker, Darrell H., et al., "Electrospinning and Nanofibers", *New Frontiers in Fiber Science, Spring Meeting,* (May 23-25, 2001).

Mattley, et al., "Light Scattering and absorption model for the quantitative interpretation of human blood platelet spectral data," Photochemisty and Photobiology, vol. 71, No. 5, May 2000, pp. 610-619.

Catalina, et al., "Quantitative spectroscopy analysis of prokaryotic cells: vegetative cells and spores," Biosensors and Bioelectronics, vol. 19, No. 8, Mar. 15, 2004, pp. 893-903.

Extended European Search Report for European Patent Application No. 09000288.2 mailed Mar. 16, 2009.

\* cited by examiner

OPTICAL METHOD AND SYSTEM TO DETERMINE DISTRIBUTION OF LIPID PARTICLES IN A SAMPLE

This application claims priority to U.S. Provisional Application No. 60/626,045 filed Nov. 8, 2004 and U.S. Provisional Application No. 60/563,614, filed Apr. 20, 2004 all of which are incorporated herein by reference.

BACKGROUND

The present invention relates to a method and system for characterizing lipoproteins in a sample, and more particularly, for characterizing lipoproteins in blood using light scattering and absorption properties of lipoproteins.

Absorption spectroscopy and light scattering methods are typically used to determine the composition and/or molecular weight of macromolecules in solution. Until recently absorption and light scattering have been considered to be separate and independent measurements even though the same physical phenomena often occur in practice for both techniques.

Absorption and light scattering measurements are usually conducted using electromagnetic energy having wavelengths in the ultraviolet to visible portion of the electromagnetic spectrum. The absorption and scattering data are typically collected by taking electromagnetic energy measurements from multiple observation angles. The theoretical background associated with absorption spectroscopy and light scattering methods is described in U.S. Pat. Nos. 6,330,058, 5,808,738 and 5,589,932, which are incorporated herein by reference. See also Alupoaei CE, et al., Biosens Bioelectron. 19, 893-903 (2004) and Alupoaei CE, et al., Biotechnol Bioeng. 86, 163-7 (2004).

Lipoproteins in blood are a heterogeneous group varying in size, composition and density. A typical lipoprotein includes a hydrophobic lipid core and a hydrophilic shell to which small proteins and other molecules are attached (usually via non-covalent interactions). The hydrophobic lipid core consists primarily of cholesterol ester and triglyceride while the hydrophilic shell consists primarily of free cholesterol and phospholipids.

Lipoproteins perform the important physiological function of delivering cholesterol and triglycerides through the endothelial lining of blood vessels to the sub-endothelial space such that the lipid components of lipoproteins form an important structural component within blood vessels. The lipoproteins circulate as small (e.g., 5 to 100 nm) insoluble particles of various densities. The densities of the lipoproteins are typically classified as very low density (VLDL), low density (LDL) and high density (HDL), although other densities are known and have been classified.

Recent medical research has shown a strong correlation between heart disease and the abundance of small LDL particles within blood. The size as well as the density of the particles has been shown to be critically important because when localized in sub-endothelial space small LDL particles can activate a strong macrophage response that leads to the formation of a therosclerotic plaque. These small LDL particles, not simply the cholesterol and triglycerides themselves, are one primary cause of coronary vascular disease.

The analysis of high and low density lipoproteins (HDL and LDL), cholesterol and triglycerides in human blood has become an important diagnostic parameter in determining the risk of cardiovascular disease. Therefore, the clinical determination of HDL, LDL, total cholesterol and triglycerides in blood has received considerable attention due to the association with human health.

Some known methods need to separate lipoprotein particles in order to determine the concentrations of HDL, LDL, total cholesterol and triglycerides in blood. Example separation techniques include precipitation and/or centrifugation in combination with enzymes conjugated to an antibody. In some forms, precipitation reagents such as polyanion-divalent cations are used to separate the VLDL and LDL from the HDL. The HDL is then analyzed via enzymatic methods and separate measurements are taken for total cholesterol and total triglyceride in order to determine LDL by an indirect approach.

There are some recent methods that have been developed using antibodies to directly determine LDL. However, these methods still require particle separation.

There are methods that do not require particle separation. As an example, a diagnostic procedure for determining a lipoprotein size and density profile using nuclear magnetic resonance is available from LipoScience, Inc., Raleigh, N.C. (http://www.liposcience.com/).

A comprehensive description of cholesterol testing can be found in the NIH publication 95-3044: "National Cholesterol Education Program, Recommendations on Lipoprotein Measurement: September 1995, with cited references inclusive as background information.

SUMMARY OF THE INVENTION

The system and method of the present invention relate to characterizing lipoproteins in a sample (e.g., a quantity of blood). In some forms, the system and method use absorption and scattering of electromagnetic energy by the lipoprotein particles at specific ultraviolet to visible wavelengths to provide a relative HDL/LDL/VLDL ratio and a particle size distribution within each density class, as well as a semi-quantitative total cholesterol and triglyceride concentration.

The system and method are effective in part because they may not require separation of the various classes of lipoprotein particles from whole blood or plasma. In some forms, the analysis may be performed on small quantities of whole blood (e.g., <10 micro liters), plasma or lipoproteins in saline.

In some forms, the system and method rely on the deconvolution of the angular and wavelength dependence of electromagnetic energy in the ultraviolet to visible range relative to scattering and absorption spectrophotometry. Different particle sizes show differences in the angular dependence of light scattering intensities. In addition, differences in the type of lipoprotein may produce differences in the absorption spectrum. Therefore, the size and type of lipoproteins in a sample may be determined by deconvoluting scattering/absorption spectra.

In one aspect, the present invention relates to a system for characterizing lipoproteins in a sample. The system includes a light source that delivers electromagnetic energy in a predetermined range of wavelengths to the sample. The system further includes a sensor that senses an intensity spectrum which emerges from the sample when sample is illuminated by the light source. A processor characterizes lipoproteins that are within in the sample by deconvoluting the intensity spectrum which emerges from the sample to determine the types of lipoproteins that are within the sample.

In another aspect, the present invention relates to a system for characterizing lipoproteins in a sample where the system includes a light source that provides electromagnetic energy to the sample in the ultraviolet to visible range. The system further includes a plurality of sensors that are disposed radially about the sample at various observation angles to simultaneously sense electromagnetic energy emerging from the sample at each observation angle. Transducers are coupled to the sensors such that each of the transducers generates a signal that is representative of an intensity spectrum for the electromagnetic energy which is detected by each of the sensors. The system further includes a processor that characterizes the lipoproteins in the sample by deconvoluting each intensity spectrum which emerges from the sample to determine the lipoproteins that are within the sample.

In still another aspect, the present invention relates to a method for characterizing lipoproteins in a sample. The method includes illuminating the sample with electromagnetic energy having a predetermined range of wavelengths and sensing the electromagnetic energy that emerges from the sample. The method further includes transducing the sensed electromagnetic energy into an intensity spectrum and determining characteristics of the lipoproteins in the sample by deconvoluting the intensity spectrum which emerges from the sample.

In yet another aspect, the present invention relates to a method for characterizing lipoproteins in a sample. The method includes illuminating the sample with electromagnetic energy having wavelengths in the ultraviolet to visible range and sensing the electromagnetic energy that emerges from the sample at a plurality of observation angles. The method further includes transducing the sensed electromagnetic energy into an intensity spectrum for each observation angle and determining characteristics of the lipoproteins in the sample by deconvoluting each intensity spectrum which emerges from the sample.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the invention.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

DETAILED DESCRIPTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
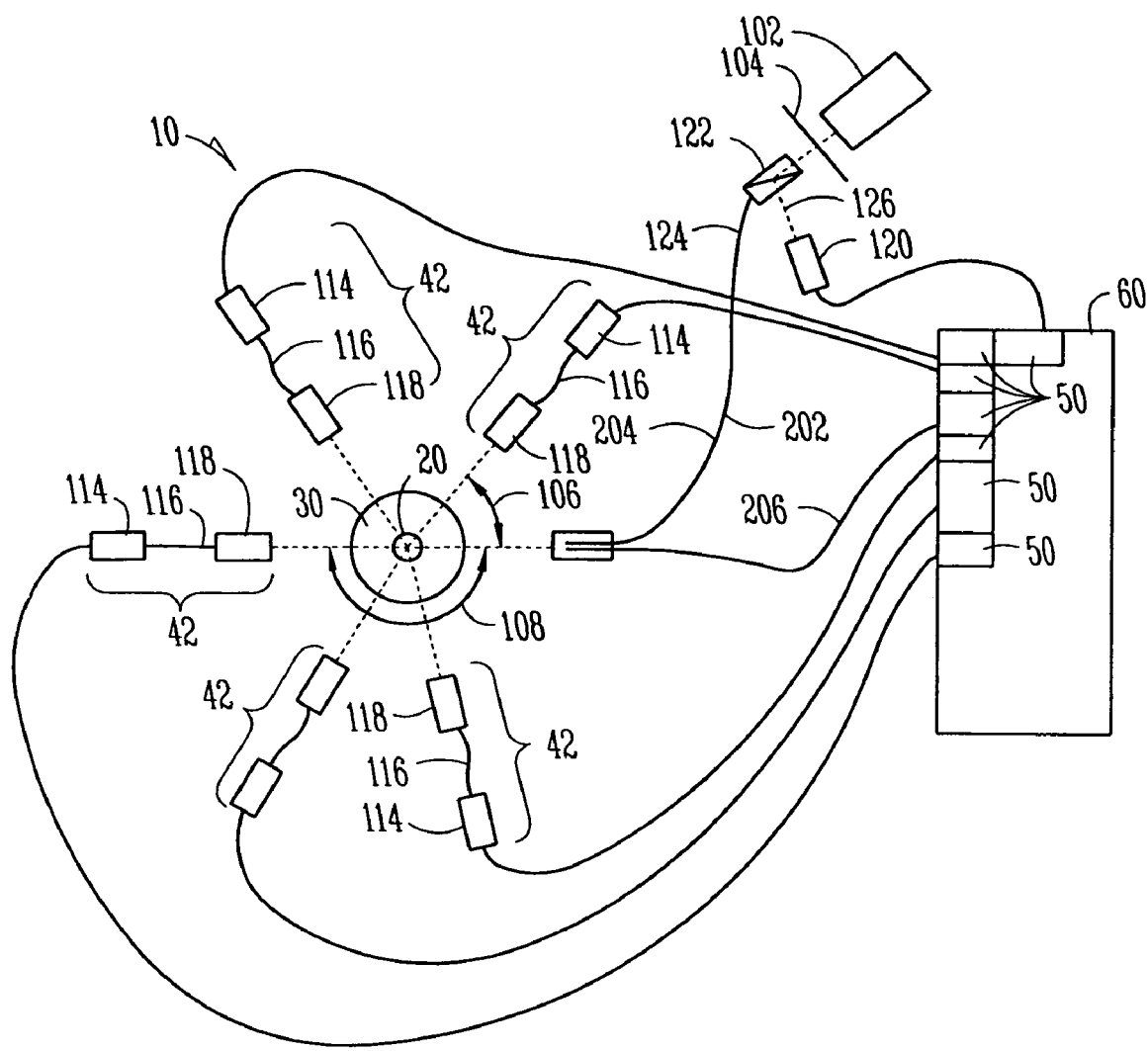
FIG. 1 is a schematic diagram of an example system for characterizing lipoproteins in a sample.

FIG. 1 schematically shows an example system 10 of the present invention. The system 10 characterizes the lipoproteins in a sample 20. In some forms, the sample 20 is contained in a cell 30 that is held in position on an optical bench. It should be noted that sample 20 may include lipoproteins in whole blood, plasma or saline. In addition, the sample 20 may be diluted and/or mixed with one or more other materials before the lipoproteins within the sample 20 are analyzed.

The system 10 includes a light source 102 that delivers electromagnetic energy to the sample 20 over a predetermined wavelength range (e.g., in the ultraviolet to visible range). In some forms, the light source 102 is a xenon light source that delivers electromagnetic energy to the sample 20 via an optical fiber 202. A polarizer 104 may be placed in the light path between the light source 102 and the sample 20 such that the sample 20 is illuminated with polarized light.

The system further includes a sensor that senses an intensity spectrum which emerges from the sample 20 when the sample 20 is illuminated by the light source 102. In the example embodiment illustrated in FIG. 1, the sensor includes a plurality of sensors 42 that are radially disposed about the sample 20 at a plurality of observation angles 106.

During operation of the system 10, one or more of the sensors 42 may be used to capture multi-angle and multi-wavelength electromagnetic energy spectra from the illuminated sample 20. Sensors 42 may be aligned to simultaneously sense electromagnetic energy that emerges from the illuminated sample 20.

Although five sensors 42 are shown in FIG. 1, it should be noted that any number of sensors 42 may be used in the system 10. The sensors 42 may be sensitive to electromagnetic energy generally in the range of 180-1000 nm. In addition, one of the sensors 42 may be placed at a 180 degree observation angle 108 relative to the electromagnetic energy that is delivered by the light source 102 in order to measure transmission and/or absorption of the electromagnetic energy by the sample 20.

In some forms, the optical fiber 202 may be a split optical fiber that includes an illumination portion 204 and a sensing portion 206. The sensing portion 206 may be positioned at a 0 degree angle relative to the electromagnetic energy that is provided by the light source 102 such that the sensing portion 206 measures backscattering of the illuminated sample 20.

In the illustrated example embodiment, each sensor 42 includes a light detector 114 (e.g., photomultipliers, photodiodes and charge-coupled devices) that receives electromagnetic energy from the illuminated sample 20. A collimating lens 118 and an optical fiber 116 may be positioned between the illuminated sample 20 and each charge-light detector 114 to produce a parallel beam of electromagnetic energy that is directed onto each light detector 114.

The system 10 may further include one or more transducers 50 that couple the sensor(s) 42 to a processor 60. Each of the transducers 50 generates a signal that represents an electromagnetic energy (i.e., intensity) spectrum as a function of wavelength for the electromagnetic energy that is sensed by each of the sensors 42. The transducers 50 may be spectrophotometer cards that are adapted to handle input from the sensors 42.

In some forms, the processor 60 receives an intensity spectrum for each observation angle as signals from each of the transducers 50. It should be noted that the processor 60 may characterize the lipoproteins in the sample 20 by deconvoluting the intensity spectrum which emerges from the sample 20 (see, e.g., deconvoluting method in U.S. Pat. No. 5,808,738, Alupoaei C E, et al., Biosens Bioelectron. 19, 893-903 (2004) and Alupoaei C E, et al., Biotechnol Bioeng. 86, 163-7 (2004)). The processor 60 may categorize the lipoproteins in the sample 20 as HDL, LDL or VLDL based on each intensity spectrum. In addition, the processor 60 may determine the relative amounts of HDL, LDL and VLDL in the sample and/or a particle size distribution for the HDL, LDL and VLDL lipoproteins in the sample.

In some forms, the system 10 compensates for fluctuations in the electromagnetic energy provided by the light source 102. As an example, the system 10 may further include a reference sensor 120 that senses electromagnetic energy which emerges directly from the light source 102. The output from the reference sensor 120 may also be fed to a spectrophotometer card 50. In the example embodiment illustrated in FIG. 1, a beam splitter 122 may be positioned between the light source 102 and the sample 20 with a first pathway 124 leading to the sample 20 and the second pathway 126 leading to the reference sensor 120.

It should be noted that the processor 60 may normalize the intensity spectra for fluctuations in the electromagnetic energy provided by the light source 102. The processor 60 utilizes the electromagnetic energy measured by reference sensor 102 to normalize the intensity spectra.

Figure 2:
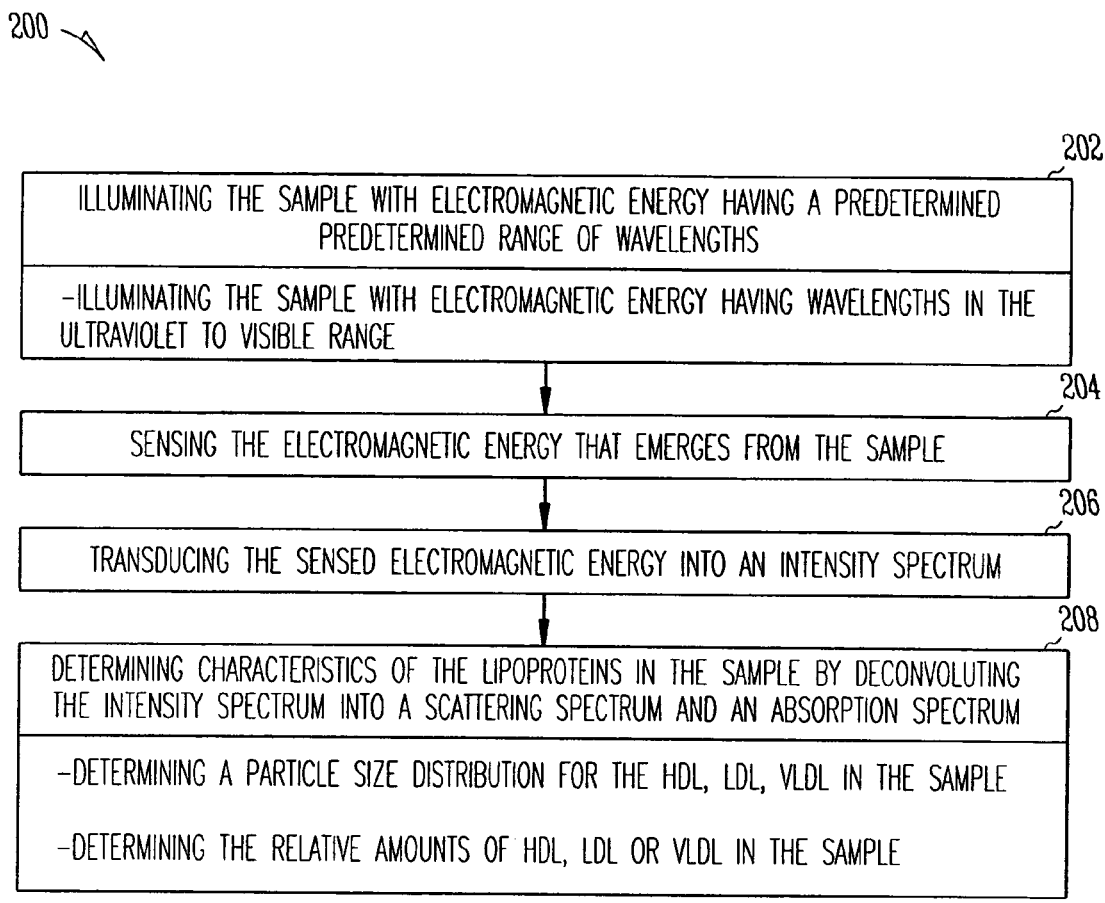
FIG. 2 illustrates an example method for characterizing lipoproteins in a sample.

FIG. 2 illustrates an example method 200 for characterizing lipoproteins in a sample. The method includes 202 illuminating the sample with electromagnetic energy having a predetermined range of wavelengths and 204 sensing the electromagnetic energy that emerges from the sample. The method further includes 206 transducing the sensed electromagnetic energy into an intensity spectrum and 208 determining characteristics of the lipoproteins in the sample by deconvoluting the intensity spectrum.

In some forms, 208 determining characteristics of the lipoproteins in the sample may include (i) determining the relative amounts of HDL, LDL and VLDL in the sample; and/or (ii) determining a particle size distribution for the HDL, LDL and VLDL lipoproteins in the sample. In addition, 202 illuminating the sample with electromagnetic energy having a predetermined range of wavelengths may include illuminating the sample with electromagnetic energy having wavelengths in the ultraviolet to visible range.

Figure 3:
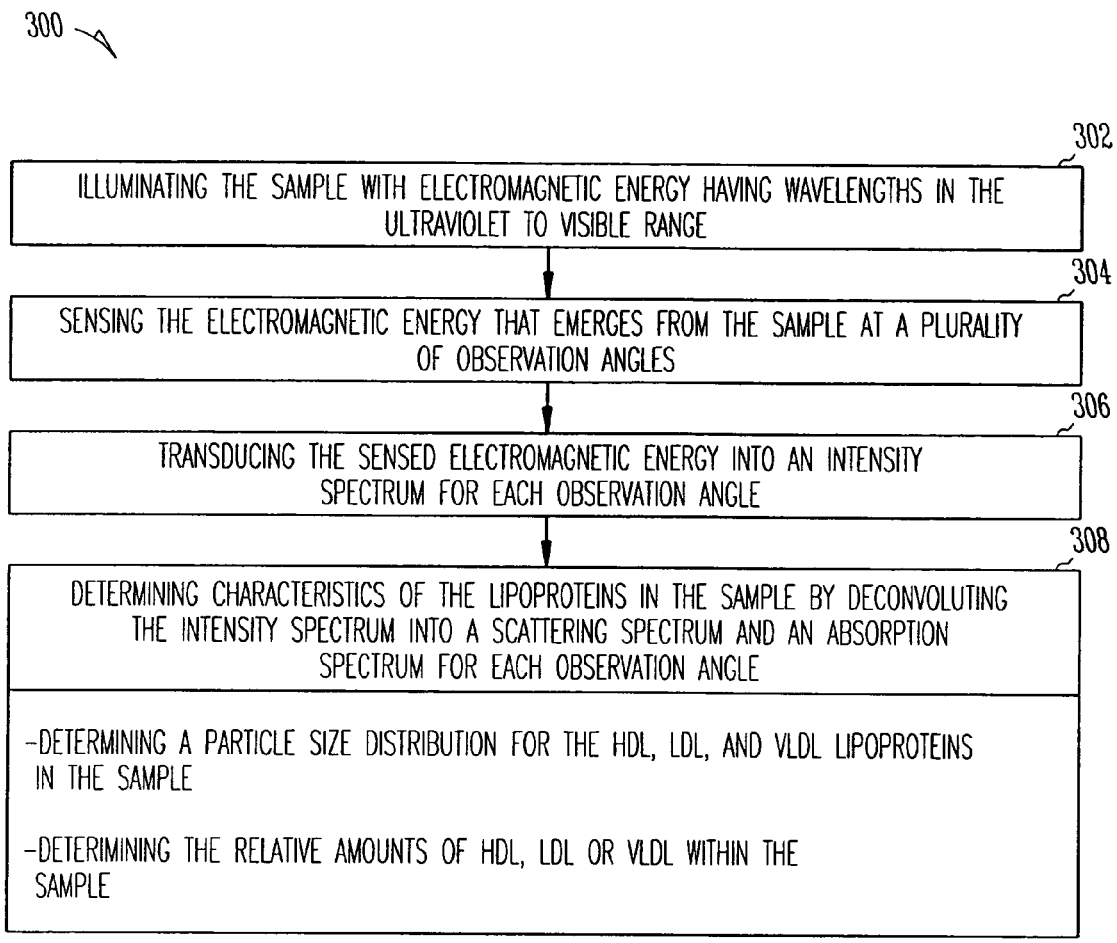
FIG. 3 illustrates another example method for characterizing lipoproteins in a sample.

FIG. 3 illustrates another example method 300 for characterizing lipoproteins in a sample. The method includes 302 illuminating the sample with electromagnetic energy having wavelengths in the ultraviolet to visible range; 304 sensing the electromagnetic energy that emerges from the sample at a plurality of observation angles; 306 transducing the sensed electromagnetic energy into an intensity spectrum for each observation angle; and 308 determining characteristics of the lipoproteins in the sample by deconvoluting each intensity spectrum. It should be noted that 308 determining characteristics of the lipoproteins in the sample may include (i) determining the relative amounts of HDL, LDL and VLDL in the sample; and (ii) determining a particle size distribution for the HDL, LDL and/or VLDL lipoproteins in the sample.

In some forms of the system and method, a light source may illuminate a continuously flowing sample. The cell for holding such a sample may include some sort of transparent piping system so that measurements may be made on the sample as the sample flows through the piping system. In another example form of the system and method, an electromagnetic field may be imposed on the sample (e.g., by a magnet) to measure the field-dependent properties of the sample.

As part of detecting lipoproteins in plasma, the scattering properties of the lipoproteins were determined using a theoretical set of optical properties. The theoretical optical properties indicated that it may be possible to discriminate the lipid fraction contained in particles with diameters in the size range 30-150 nm.

EXAMPLE

A purified fraction of Lp(a) particles was obtained in a 1 mL sample. Intensity spectra of the Lp(a) fraction were obtained by illuminating the sample as described above. The spectra were measured as a function of the particle concentration by recording in an Hp-8454 diode array spectrophotometer using a 1 cm path length micro-cuvette. Standard buffer saline was used as a diluent.

A set of optical properties was derived from the intensity spectra. The optical properties of the sample confirmed a portion of the theoretical optical properties that were previously determined.

Figure 4:
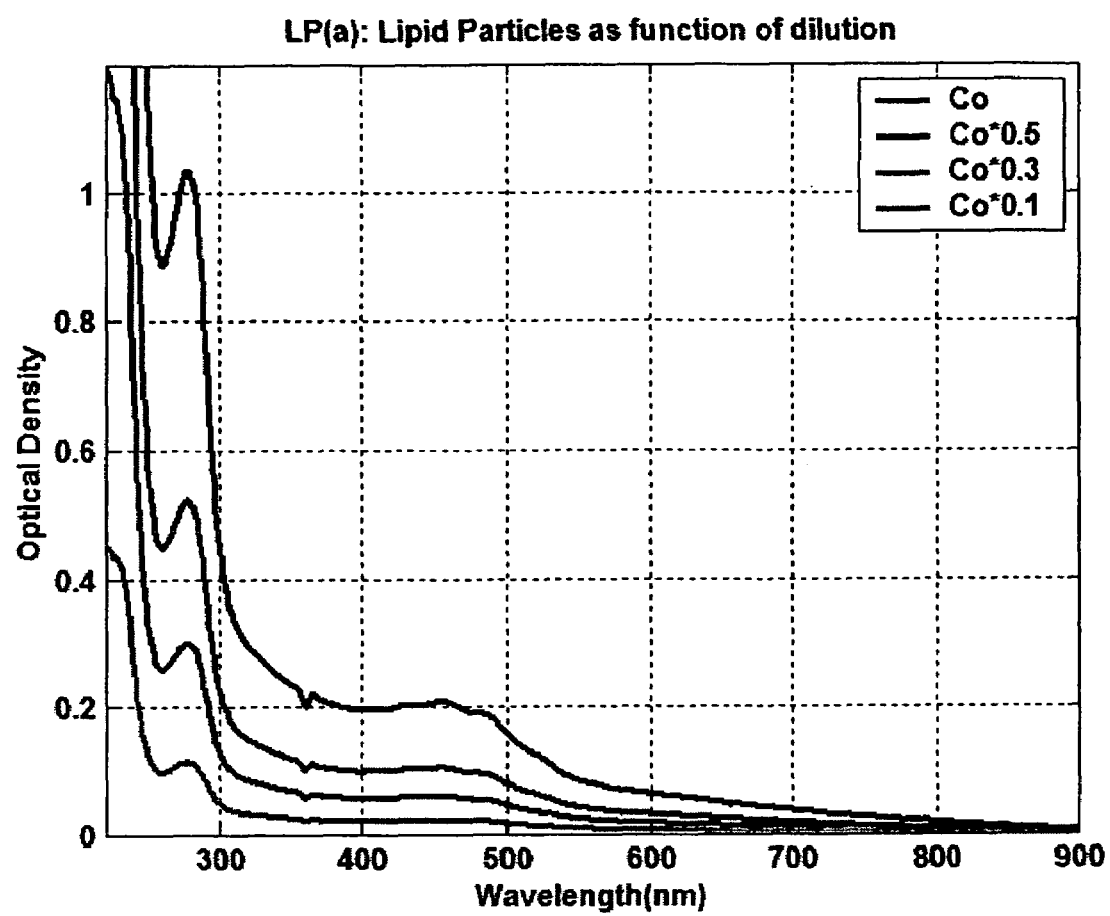
FIG. 4 shows Uv-vis spectra of a purified Lp(a) as a function of dilution.
Figure 5:
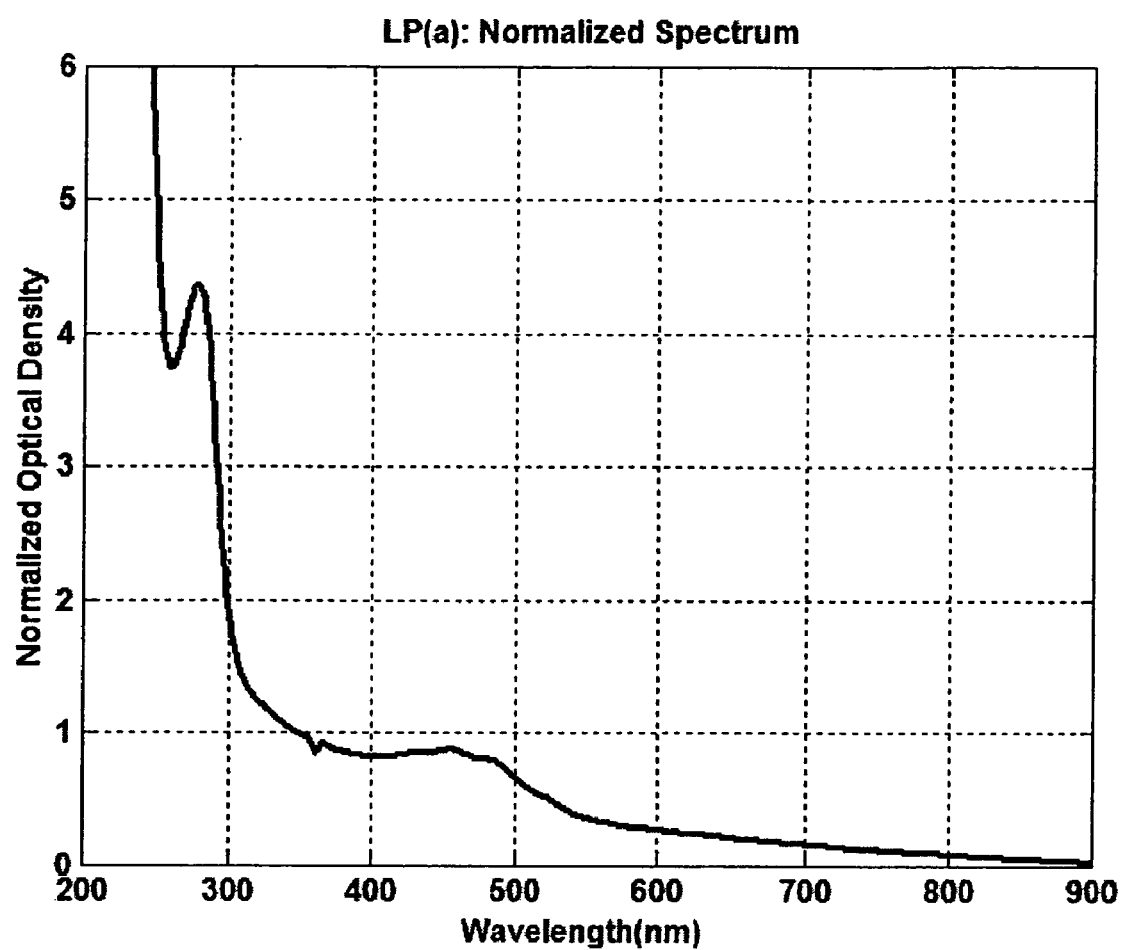
FIG. 5 shows the Uv-vis spectra of FIG. 4 normalized.

FIG. 4 shows the measured spectra of the purified Lp(a) sample as function of concentration while FIG. 5 shows the normalized optical density spectrum for the sample. The normalization of the spectra eliminates the effect of the number of particles (as explained in C. E Alupoaei, J. A. Olivares, and L. H. Garcia-Rubio, "*Quantitative Spectroscopy Analysis of prokaryotic Cells: Vegetative Cells and Spores*", Biosensors and Bioelectronics, 2004, 19(8), 893-903).

The optical properties of the Lp(a) fraction were estimated from the spectra shown in FIG. 4 using the Kramers-Kronig transforms. The optical properties established the possibility of deconvoluting the presence of the LDL, HDL, and VLDL lipoprotein particles from measurements of the plasma spectrum.

Figure 6:
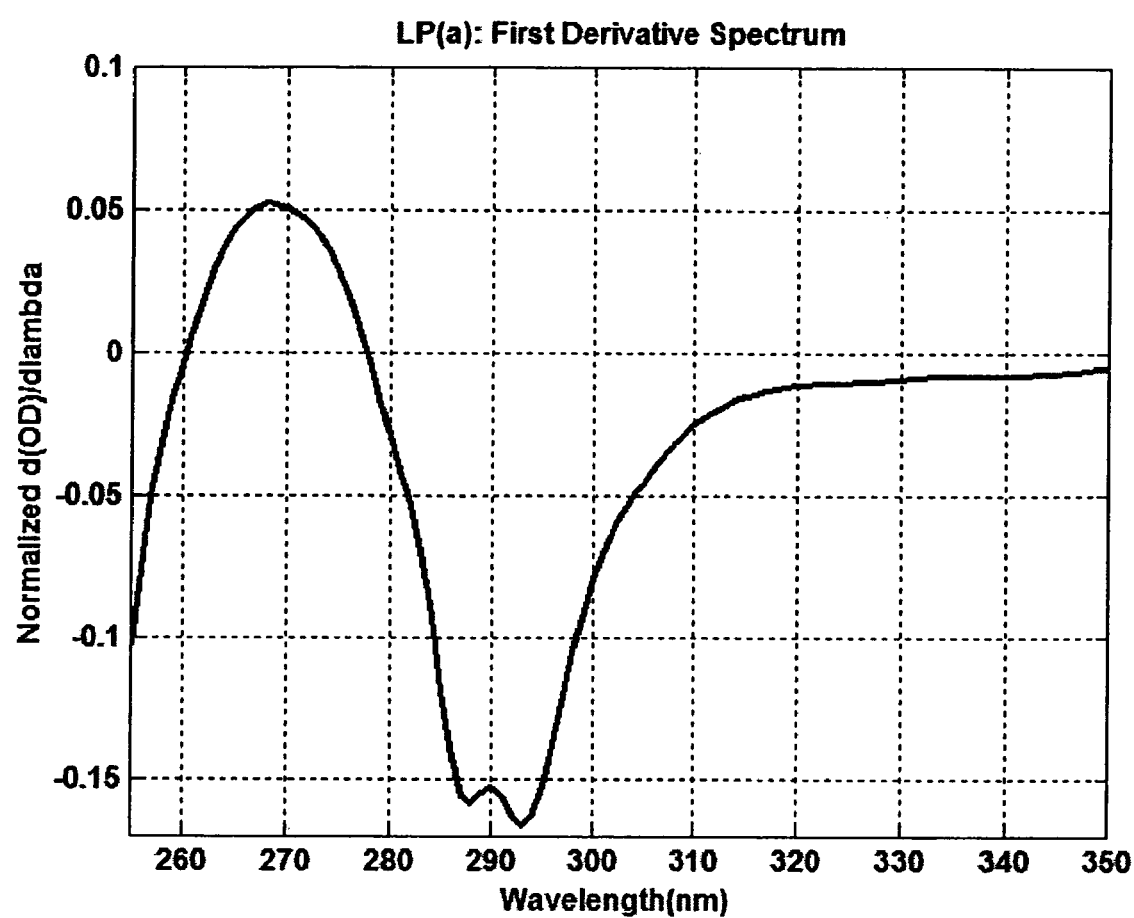
FIG. 6 shows a derivative of the normalized Uv-vis spectrum of FIG. 5.

FIG. 6 shows the derivative spectrum of the spectrum shown in FIG. 5 where the chromophoric amino acids of proteins absorb tyrosine, tryptophan and phenyl alanine. The absorption band at 280 nm is typically used to estimate the protein content of a sample.

Figure 7:
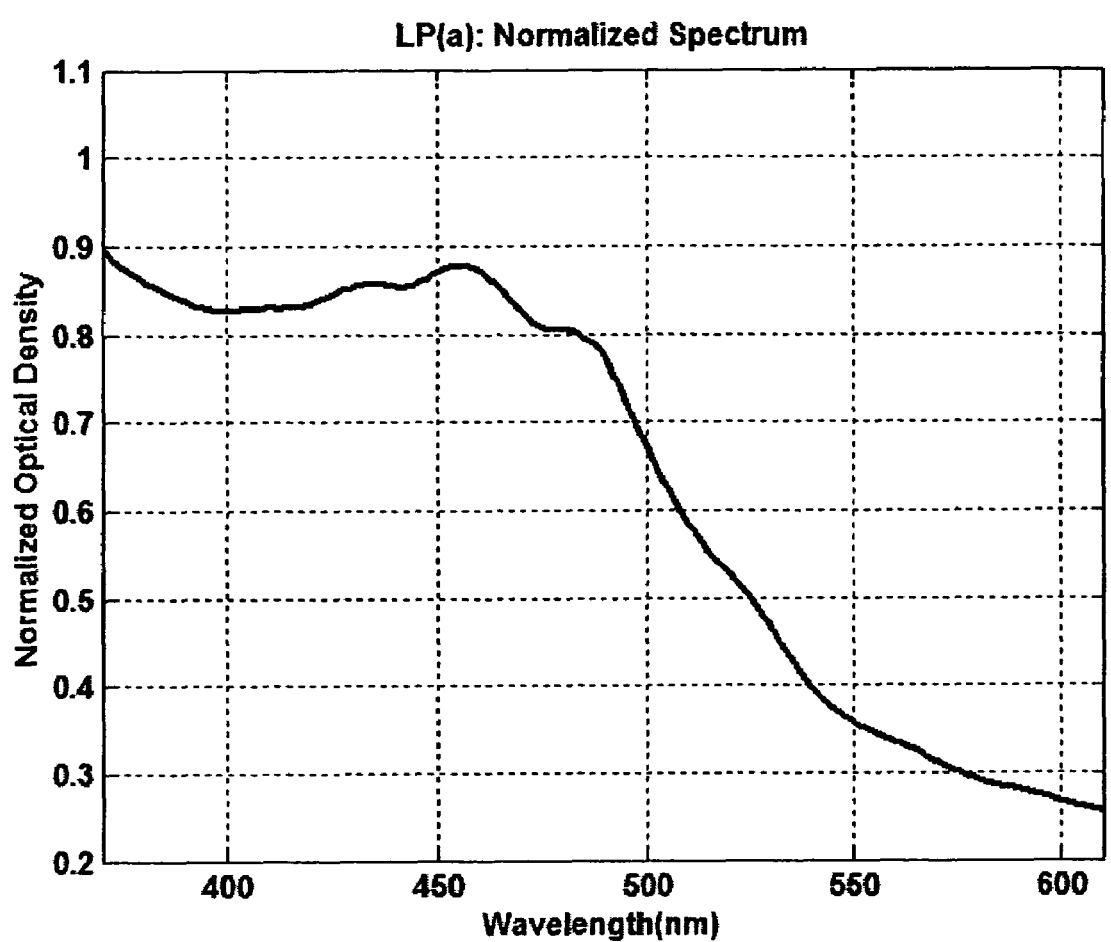
FIG. 7 shows a magnification of the normalized Uv-vis spectrum illustrated in FIG. 5.
Figure 8:
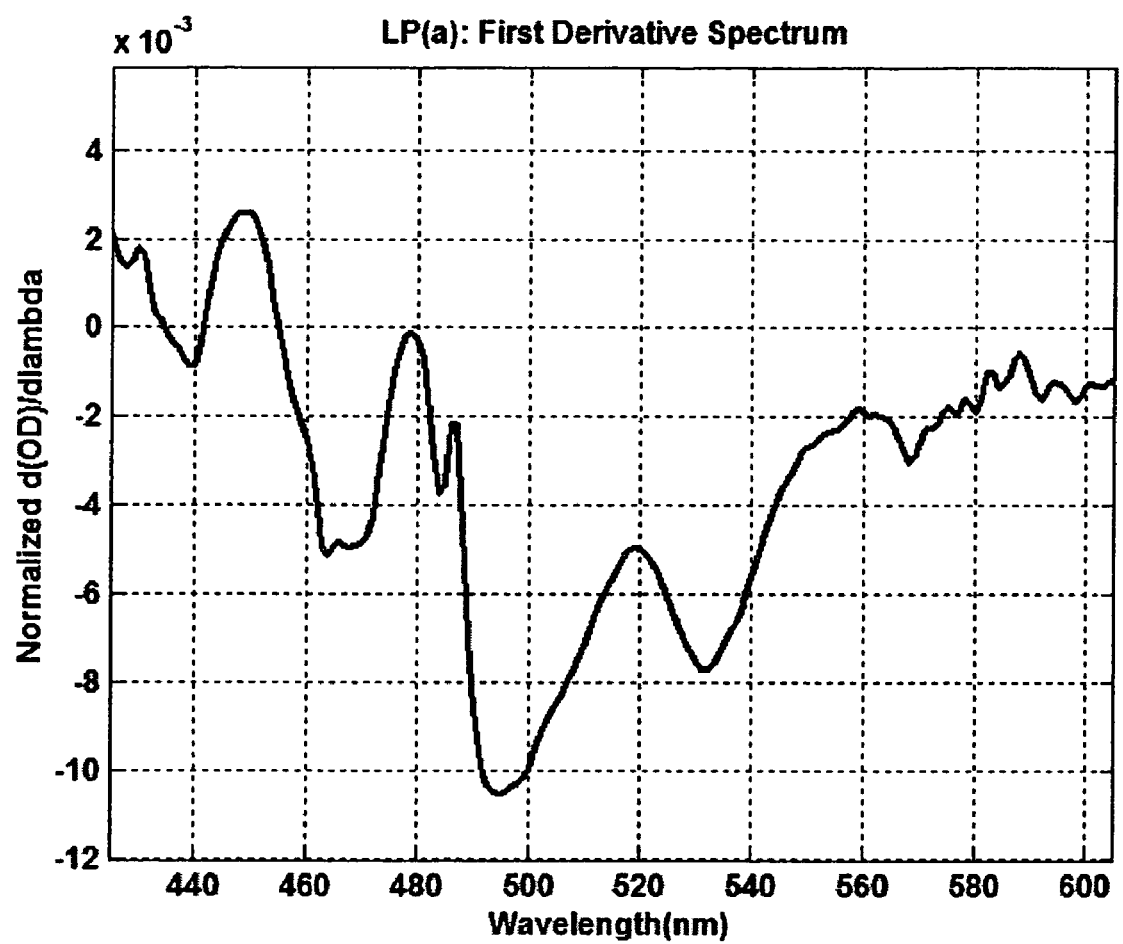
FIG. 8 shows a derivative of the magnified Uv-vis spectrum illustrated in FIG. 7.

FIGS. 7-8 show a magnification of the spectrum shown in FIG. 5. FIG. 7 shows a distinct absorption pattern while FIG. 8 shows its corresponding derivative.

In addition, previously measured spectra of plasma samples (S. Narayanan, Ph. D. Dissertation, University of South Florida, 1999, unpublished results; Y. Mattley, Ph. D. Dissertation, University of South Florida, 2000, and Y. Mattley, G. Leparc, R. Potter, and L. H. Garcia-Rubio, "Light Scattering and Absorption Model for the Quantitative Interpretation of Human Platelet Spectral Data", Photochemistry and Photobiology, 2000, 71(5)), were deconvoluted using software.

Figure 9:
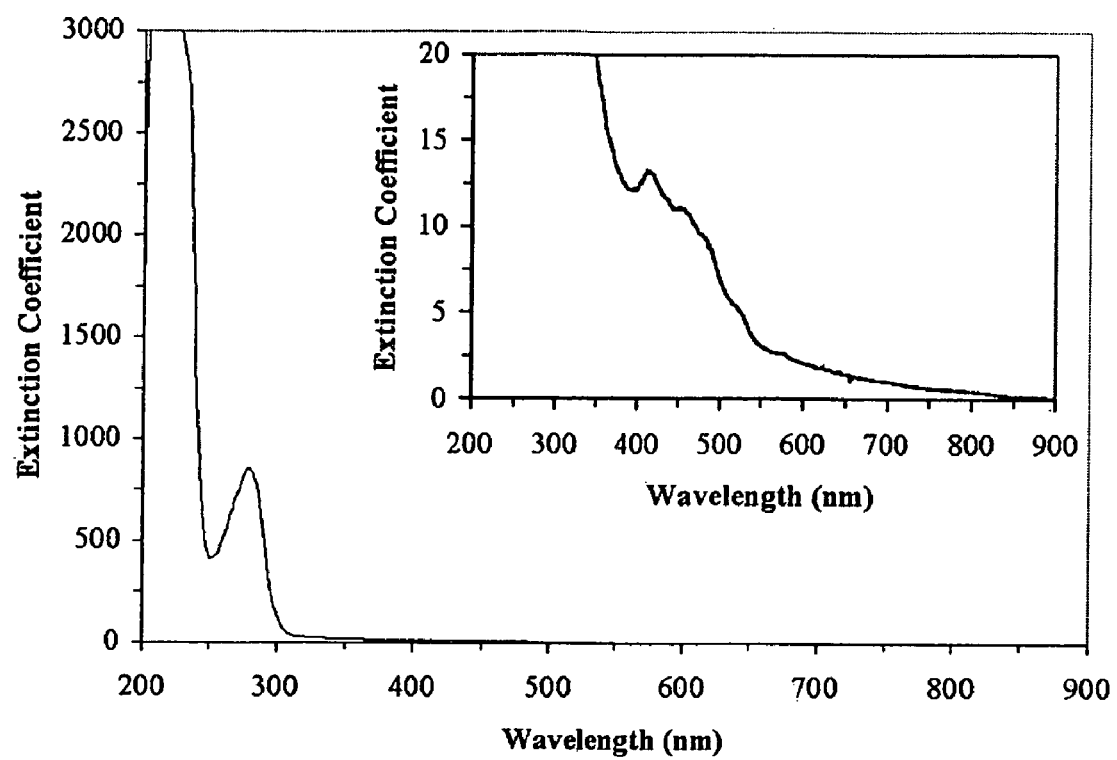
FIG. 9 shows a Uv-vis spectrum of a sample of plasma as function of wavelength with an inset figure that is an enlargement of the region from 300 to 700 nm.
Figure 10:
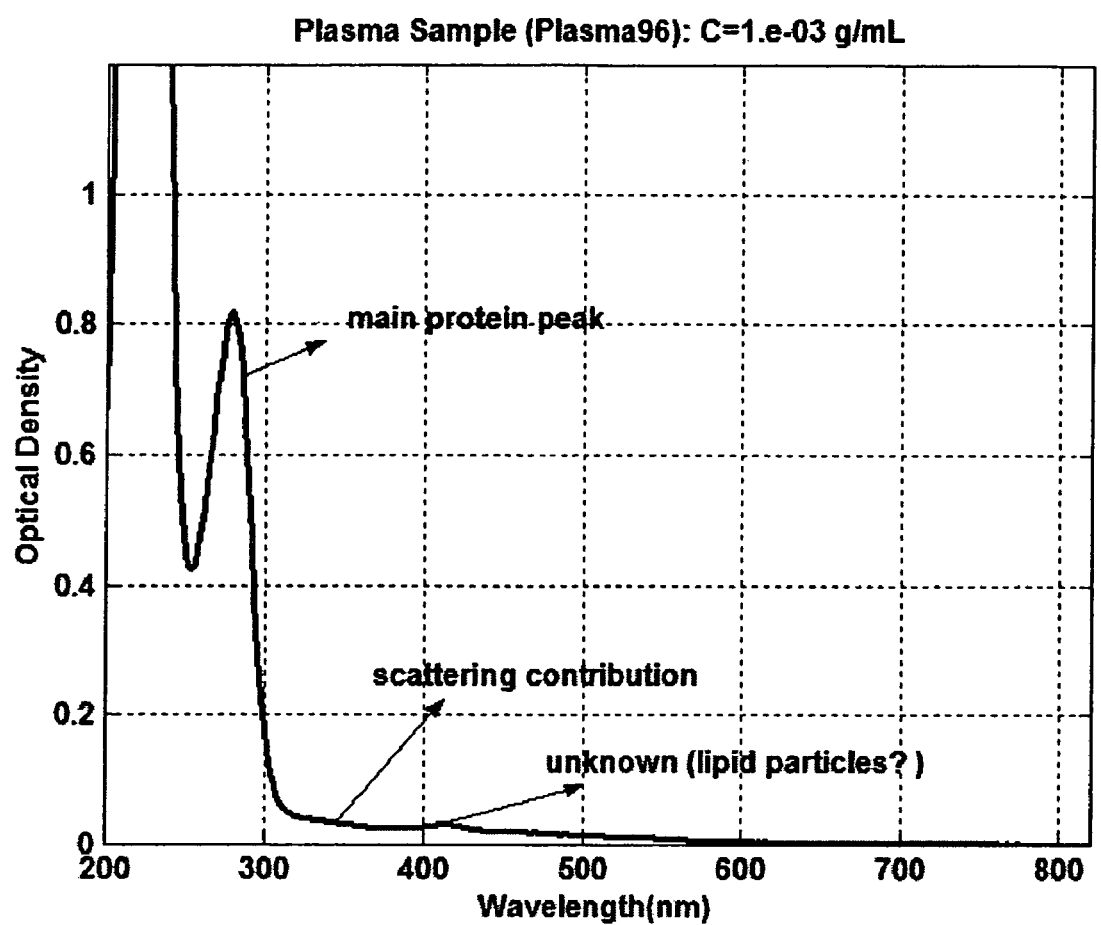
FIG. 10 shows a Uv-vis spectrum of plasma as function of wavelength with portions of the spectrum identified relative to some of the constituents in the sample.
Figure 11:
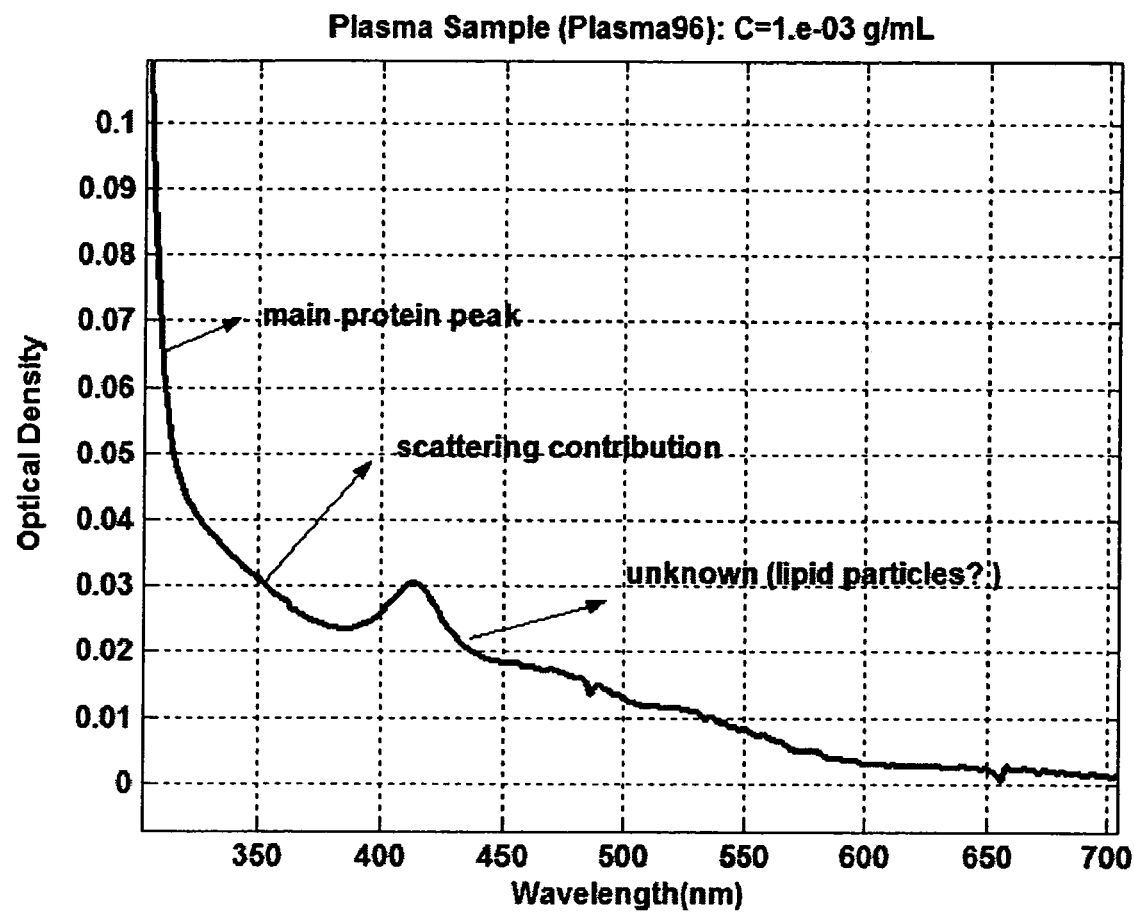
FIG. 11 shows a magnification of the Uv-vis spectrum illustrated in FIG. 10.

A comparison of the deconvoluted spectra and the optical properties of the sample establish that (i) there are distinct spectral features in the Lp(a) fraction (e.g., in the 350-600 nm range) which identify this particular fraction (and possibly other fractions); (ii) plasma includes detectable particle populations in the approximate size range of LDL, HDL, and VLDL lipoprotein particles; and (iii) the spectra of the lipoprotein particles is present in varying proportions in the spectra of the analyzed plasma samples (see, e.g., FIGS. 9-11). FIG. 9 is similar to FIG. 7 and can be found in Y. Mattley, Ph. D. Dissertation, University of South Florida, 2000, and Y. Mattley, G. Leparc, R. Potter, and L. H. Garcia-Rubio, "Light Scattering and Absorption Model for the Quantitative Interpretation of Human Platelet Spectral Data", Photochemistry and Photobiology, 2000, 71(5)). In addition, FIG. 10 can be found in S. Narayanan, Ph. D. Dissertation, University of South Florida, 1999.

Figure 12:
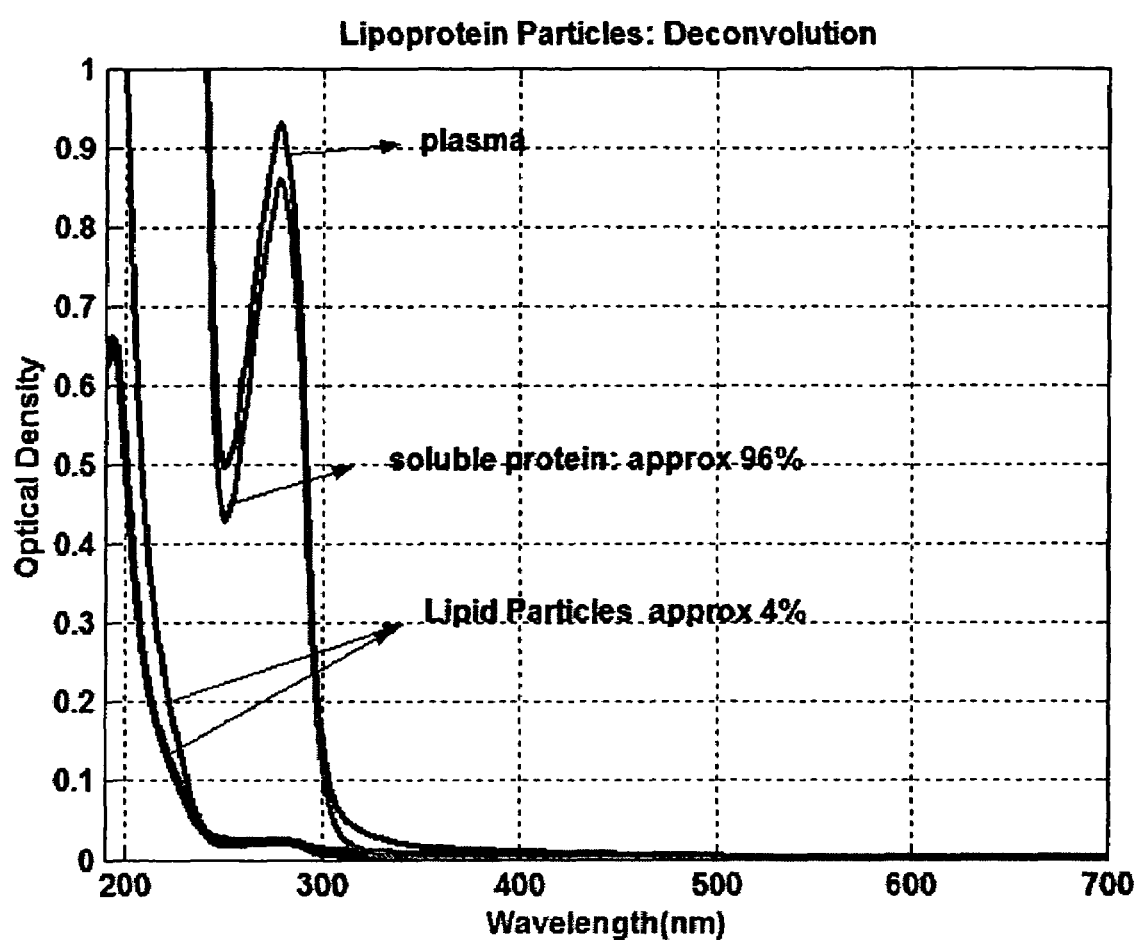
FIG. 12 shows a comparison between the measured spectrum of a plasma sample and calculated spectra of contributions in the sample from soluble protein and lipid particles.
Figure 13:
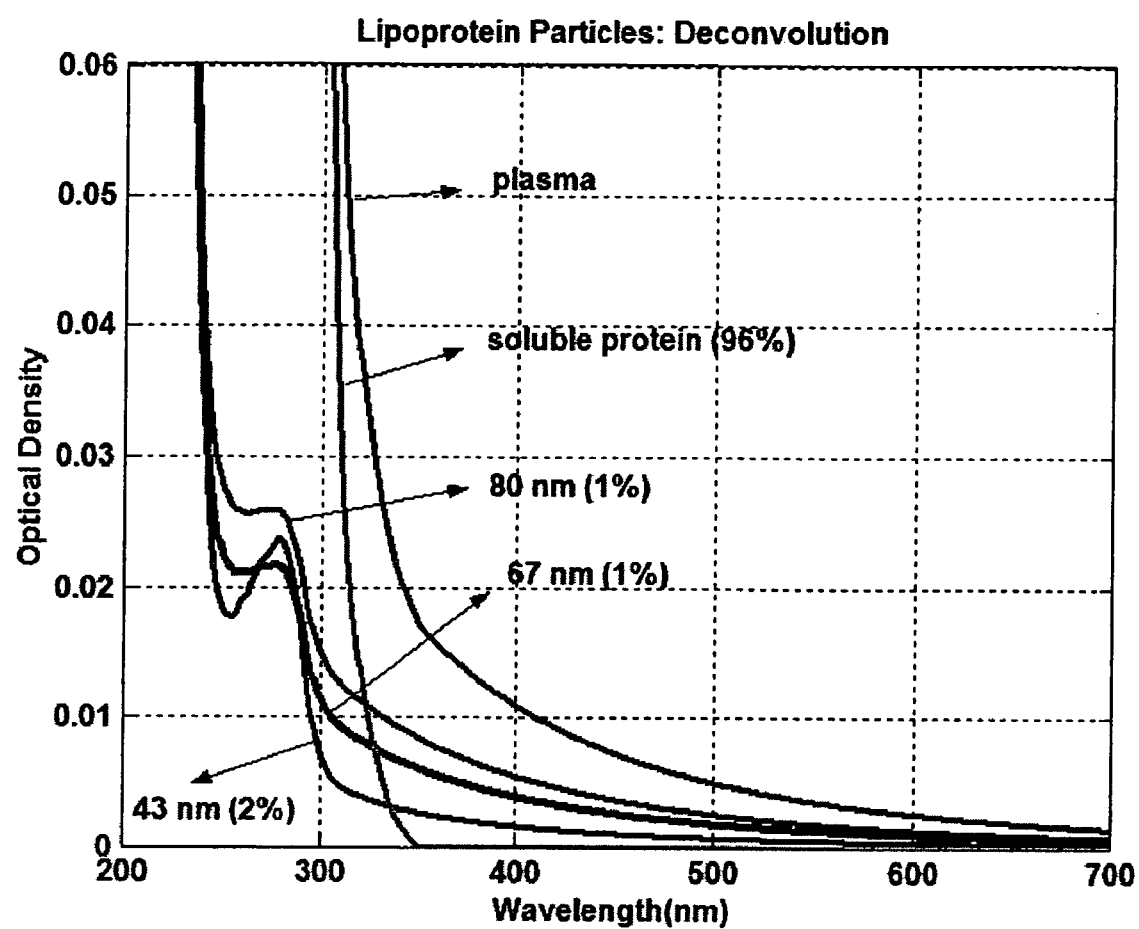
FIG. 13 shows a magnification of the measured spectra and calculated spectra illustrated in FIG. 12.

The spectra of previously measured plasma samples were analyzed using deconvolution software. FIGS. 12-13 show the deconvolution of the spectra in terms of the lipid particles. The deconvolution establishes that the spectral measurements contain information on the LDL, HDL, and VLDL lipoprotein particles.

The results indicate that the fraction of lipid particles within a sample may be estimated from transmission and angular scattering measurements. Furthermore, the presence of an Lp(a) fraction can be identified in a plasma sample from the spectral signature of the sample.

The operations discussed above with respect to the described methods may be performed in a different order from those described herein. While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

We claim:

1. A system for characterizing lipoproteins in a sample, the system comprising:
    a whole blood or plasma sample containing lipoproteins
    a light source to provide electromagnetic energy in the ultraviolet to visible range to the sample;
    a sensor that senses an intensity spectrum which emerges from the sample; and
    a processor that characterizes lipoproteins in the sample by deconvoluting the intensity spectrum which emerges from the sample into a scattering spectrum and an absorption spectrum.

2. The system of claim 1 further comprising a transducer coupled to the sensor, the transducer sending signals to the processor that represent the intensity spectrum which emerges from the sample.

3. The system of claim 2, wherein the transducer includes a spectrophotometer card that is coupled to the processor and the sensor.

4. The system of claim 1, wherein the processor normalizes the intensity spectrum for intensity fluctuations in the electromagnetic energy provided by the light source.

5. The system of claim 1, wherein the sensor includes a charge-coupled device.

6. The system of claim 5, further comprising a collimating lens optically coupled with the charge-coupled device, the collimating lens being positioned between the sample and the charge-coupled device to produce parallel beams of electromagnetic energy from the electromagnetic energy emitted from the sample.

7. The system of claim 1, wherein the processor determines the relative amounts of HDL, LDL and VLDL lipoproteins in the sample.

8. The system of claim 7, wherein the processor determines a particle size distribution for the HDL, LDL and VLDL lipoproteins in the sample.

9. A system for characterizing lipoproteins in a sample, the system comprising:
    a whole blood or plasma sample containing lipoproteins
    a light source that provides electromagnetic energy in the ultraviolet to visible range to the sample;
    a plurality of sensors disposed radially about the sample at various observation angles to sense electromagnetic energy emerging from the sample at each observation angle;
    a plurality of transducers coupled to the plurality of sensors, each of the transducers generating signals that are representative of an intensity spectrum for the electromagnetic energy that is detected by each of the sensors; and
    a processor that characterizes the lipoproteins in the sample by deconvoluting each intensity spectrum which emerges from the sample into a scattering spectrum and an absorption spectrum.

10. The system of claim 9, wherein the processor determines the relative amounts of HDL, LDL and VLDL in the sample.

11. The system of claim 9, wherein the processor determines a particle size distribution for HDL, LDL and VLDL lipoproteins present in the sample.

12. A method for characterizing lipoproteins in a sample, the method comprising:
    illuminating the sample with electromagnetic energy having wavelengths in the ultraviolet to visible range;
    sensing the electromagnetic energy that emerges from the sample;
    transducing the sensed electromagnetic energy into an intensity spectrum; and
    determining characteristics of the lipoproteins in the sample by deconvoluting the intensity spectrum that emerges from the sample into a scattering spectrum and an absorption spectrum; wherein the sample includes lipoproteins in whole blood or plasma.

13. The method of claim 12 wherein determining characteristics of the lipoproteins in the sample includes determining the relative amounts of HDL, LDL and VLDL in the sample.

14. The method of claim 12 wherein determining characteristics of the lipoproteins in the sample includes determining a particle size distribution for HDL, LDL and VLDL lipoproteins present in the sample.

15. A method for characterizing lipoproteins in a sample, the method comprising:
    illuminating the sample with electromagnetic energy having wavelengths in the ultraviolet to visible range;
    sensing the electromagnetic energy that emerges from the sample at a plurality of observation angles;
    transducing the sensed electromagnetic energy into an intensity spectrum for each observation angle; and
    determining characteristics of the lipoproteins in the sample by deconvoluting each intensity spectrum that emerges from the sample into a scattering spectrum and an absorption spectrum; wherein the sample includes lipoproteins in whole blood or plasma.

16. The method of claim 15 wherein determining characteristics of the lipoproteins in the sample includes determining the relative amounts of HDL, LDL and VLDL in the sample.

17. The method of claim 15 wherein determining characteristics of the lipoproteins in the sample includes determining a particle size distribution for HDL, LDL and VLDL lipoproteins present in the sample.

18. A system for characterizing lipoproteins in a sample, the system comprising:
 a whole blood or plasma sample containing lipoproteins
 a light source that provides electromagnetic energy in the ultraviolet to visible range to the sample;
 a sensor that senses an intensity spectrum which emerges from the sample; and
 a processor that determines a particle size distribution for HDL, LDL, and VLDL lipoproteins in the sample by deconvoluting the intensity spectrum which emerges from the sample into a scattering spectrum and an absorption spectrum.

19. A method for characterizing lipoproteins in a sample, the method comprising:
 illuminating the sample with electromagnetic energy having wavelengths in the ultraviolet to visible range;
 sensing the electromagnetic energy that emerges from the sample;
 transducing the sensed electromagnetic energy into an intensity spectrum;
 determining a particle size distribution for HDL, LDL, and VLDL lipoproteins in the sample by deconvoluting the intensity spectrum that emerges from the sample into a scattering spectrum and an absorption spectrum;
 wherein the sample includes lipoproteins in whole blood or plasma.

* * * * *